US007341985B2

(12) United States Patent
Lal et al.

(10) Patent No.: US 7,341,985 B2
(45) Date of Patent: Mar. 11, 2008

(54) 2-HYDROXY-3-ALKOXYPROPYL SULFIDES, SULFONES, AND SULFOXIDES: NEW SURFACE ACTIVE AGENTS

(75) Inventors: Gauri Sankar Lal, Whitehall, PA (US); Williams Rene Edouard Raymond, New Tripoli, PA (US); Khalil Yacoub, Allentown, PA (US); Evelyn Jennifer Lin Paulsen, Macungie, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 376 days.

(21) Appl. No.: 10/961,763

(22) Filed: Oct. 8, 2004

(65) Prior Publication Data

US 2006/0079431 A1 Apr. 13, 2006

(51) Int. Cl.
*C11D 1/12* (2006.01)
*C11D 3/34* (2006.01)
*C07C 319/00* (2006.01)
*C07C 317/00* (2006.01)

(52) U.S. Cl. .................. 510/414; 510/426; 510/492; 510/505; 568/38; 568/39; 568/45; 568/300; 568/579

(58) Field of Classification Search ............... 568/38, 568/39, 45, 300, 579; 510/414, 426, 492, 510/505
See application file for complete search history.

(56) References Cited

U.S. PATENT DOCUMENTS

| 3,505,320 | A | 4/1970 | Dabritz et al. |
| 3,954,839 | A | 5/1976 | Dexter et al. |
| 4,036,974 | A | 7/1977 | Walker et al. |
| 4,095,029 | A | 6/1978 | Fields |
| 6,177,469 | B1 | 1/2001 | Zilch et al. |
| 7,049,472 | B2 * | 5/2006 | Lal et al. ............... 564/463 |
| 7,205,431 | B2 * | 4/2007 | Lal et al. ............... 562/18 |

FOREIGN PATENT DOCUMENTS

| DE | 2730414 | * | 1/1978 |
| EP | 0 742 259 B1 | | 10/2000 |
| EP | 1 624 048 A1 | | 2/2006 |
| GB | 1120652 | | 7/1968 |
| GB | 1 394 354 | | 5/1975 |
| GB | 1 532 070 | | 11/1978 |
| GB | 2 160 521 A | | 12/1985 |
| JP | 4-145094 | | 5/1992 |

OTHER PUBLICATIONS

Kuliev, A.M., et al., "Synthesis of S-beta-hydroxy-gamma-alkoxypropyl-substituted thiophenols," No. 5-6, pp. 44-46 (1971)—Abstract (XP009062967), no month given.
Mlotkowska, B., et al., "A Synthesis of rac-S-(2-Acetoxy-3-hexadecyloxypropyl) Thiophosphcholine, the Isosteric and Isopolar PAF Analog," *Liebigs Ann.*, No. 8, pp. 1467-1470 (1995), no month given.
Derzhinskii, A.R., et al., "Functional Sulfur-Containing Compounds. Communication 7, Reactions of 2,3-Epoxypropyl Alkyl Sulfides, Sulfoxides, and Sulfones with Alkoxides and Amines," *Bulletin of the Academy of Sciences of the USSR*, Division of Chemical Science, vol. 34, No. 7, pp. 1484-1494 (1985), no month given.
Atavin, A.S., et al., "Vinyl Esthers Containing the Epoxy Group V. Synthesis From 2-(Vinyloxyalkoxymethyl) Oxiranes," *Journal of Organic Chemistry of the USSR*, vol. 6, No. 2, pp. 214-219 (1970), no month given.
Rietz, E.G., et al., "Derivatives of Beta-Hydroxypopyl Sulfides. II. Alkylthioalkoxypropanols," *Journal of the American Chemical Society*, vol. 74, No. 5, pp. 1358-1359 (1952), no month given.
Byun, H-S., et al., "A Short Synthesis of Antitumor Ether Thioglycolipids: Thioglycosidation of a Glucose Donor with a Tributylstannyl Sulfide Acceptor," *Tetrahedron Letters*, vol. 36, No. 29, pp. 5143-5146 (1995), no month given.
Nishikubo, T., et al., "New Catalytic Activity of Polymer-Supported Quaternary Onium Salts. Regioselective Addition Reaction of Oxiranes with Active Esters Catalyzed by Insoluble Polystyrene-Bound Quaternary Ammonium and Phosphonium Salts," *Journal of Organic Chemistry*, vol. 55, pp. 2536-2542 (1990), no month given.
Khosropour, A.R., et al., "Zn/CeCl$_3$. 7H$_2$ O-TBPB: A New and 'Green' Promoter System for Rapid and Regioselective Thiolyzation of 1,2-Epoxides with Aryl Disulfides," *Chemistry Letters*, vol. 33, No. 10, pp. 1378-1379 (2004), no month given.
European Search Report No. 05021711.6 dated Mar. 24, 2006.

* cited by examiner

*Primary Examiner*—Brian Mruk
(74) *Attorney, Agent, or Firm*—Michael Leach

(57) ABSTRACT

Compositions containing surfactant compounds according to formula (I)

$$R_4OCH_2CH(OH)CR_2R_3ZR_1 \qquad (I)$$

wherein Z is S, SO, or SO$_2$, can have a range of equilibrium and/or dynamic surface tensions and a range of foaming performance attributes, depending upon the particular values of Z, $R_1$, $R_2$, $R_3$, and $R_4$. The compounds of formula (I) may be prepared by a process that includes reaction of a thiol with a glycidyl ether.

33 Claims, No Drawings

2-HYDROXY-3-ALKOXYPROPYL SULFIDES, SULFONES, AND SULFOXIDES: NEW SURFACE ACTIVE AGENTS

FIELD OF THE INVENTION

This invention relates to surfactant compositions. More particularly, it relates to adducts of thiols with glycidyl ethers and their use to reduce the surface tension in water-based systems.

BACKGROUND OF THE INVENTION

The ability to reduce the surface tension of water is of great importance in the application of water-based formulations because decreased surface tension translates to enhanced substrate wetting during use. Examples of water-based compositions requiring good wetting include coatings, inks, adhesives, fountain solutions for lithographic printing, cleaning compositions, metalworking fluids, agricultural formulations, electronics cleaning and semiconductor processing compositions, personal care products, and formulations for textile processing and oilfield applications. Surface tension reduction in water-based systems is generally achieved through the addition of surfactants, resulting in enhanced surface coverage, fewer defects, and more uniform distribution. Equilibrium surface tension (EST) is important when the system is at rest, while dynamic surface tension (DST) provides a measure of the ability of a surfactant to reduce surface tension and provide wetting under high speed application conditions.

The importance of the ability of a surfactant to achieve low surface tension at low use levels, the ability to affect foaming performance, and the surfactant's ability to provide efficient emulsification and solubilization are all of considerable industrial importance, as is well-appreciated in the art. And, although equilibrium surface tension reduction efficiency is important for some applications, other applications may require both equilibrium and dynamic surface tension reduction.

The foaming characteristics of a surfactant are also important because they can help define applications for which the surfactant might be suitable. For example, foam can be desirable for applications such as ore flotation and cleaning. On the other hand, in coatings, graphic arts and adhesive applications, foam is undesirable because it can complicate application and lead to defect formation. Thus foaming characteristics are frequently an important performance parameter.

The wide variety of applications for which surfactants are used, and the resultant variation in performance requirements, results in a need for a correspondingly large number of surfactants adapted to these various performance demands, and a need for suitable methods for making them.

SUMMARY OF THE INVENTION

In a first aspect, the invention provides a composition including a compound according to formula (I)

$$R_4OCH_2CH(OH)CR_2R_3ZR_1 \qquad (I).$$

In formula (I), $R_4$ is selected from the group consisting of C3-C30 branched, linear, and cyclic alkyl, alkenyl, aryl, and aralkyl moieties; C3-C30 branched, linear, and cyclic alkyl, alkenyl, aryl, and aralkyl moieties bearing a carbonyl group or one or more heteroatoms selected from O, S, and N; glycol ether moieties of the formula $R_5(OCH_2CH_2)_q$—; aminoethylene moieties of the formula $R_5(NHCH_2CH_2)_q$—; and thioether moieties of the formula $R_5S(CH_2)_q$—; wherein $R_5$ is H or linear C1-C12 alkyl. $R_2$ and $R_3$ are each independently selected from the group consisting of H and linear or branched C1-C3 alkyl and alkenyl groups. $R_1$ is selected from the group consisting of C3-C16 linear, cyclic, and branched alkyl, alkenyl, aryl, aralkyl, and alkaryl moieties, and any of these moieties substituted with carboxy, sulfo, or phospho substituents;
—$CH_2(CHOH)_nCH_2OH$;
—$(CH_2)_2O(CH_2)_2T$;
—$(CH_2)_mT$; and
—$CH_2CH(OH)CH_2(C_3H_6O)_pO$—$R(O(C_3H_6O)_p$
$CH_2CHOHCH_2T)_2$.

In the above structures, m is an integer from 2 to 4, n is an integer from 0 to 5, p is 1 or 2; q is an integer from 1 to 15, T is SH or $ZCR_2R_3CH(OH)CH_2OR_4$, R is a trimethylolpropane- or glycerol-based segment, and Z is S, SO, or $SO_2$, provided that Z is not S when $R_1$ is —$CH_2(CHOH)_nCH_2OH$.

In a second aspect, the invention provides a method of preparing a compound according to formula (I) above, the method including contacting at least one compound according to formula (II)

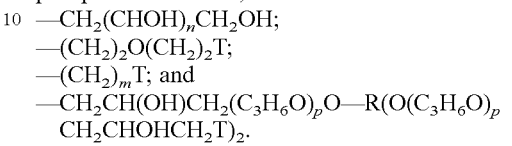

with a mercaptan $R_1$—SH, wherein $R_1$, $R_2$, $R_3$, and $R_4$ are as defined above.

In a third aspect, the invention provides a formulation including between 0.1 and 99.9 wt % in total of one or more ingredients selected from surfactants and wetting agents other than according to formula (I); solvents; alkali metal hydroxides; water-borne, water-dispersible, or water-soluble resins; flow agents; leveling agents; pigments; processing aids; defoamers; solubilizing agents; pesticides; plant growth modifying agents; water-soluble film-forming macromolecules; water-soluble alcohols, glycols, or polyols; water-soluble acids or salts thereof; tetramethylammonium hydroxide; emulsifying agents; alkanolamines; organic monoacids; biocides; chelants; detergent builders; detergent co-builders; dyes; fragrances; anti-redeposition aids; sunscreen agents; solubilizing agents; polymers; oligomers; functional cement additives; and water. The formulation also includes between 0.001 and 45 wt % of one or more compounds according to formula (I) as defined above, wherein however Z may also be S when $R_1$ is —$CH_2(CHOH)_nCH_2OH$.

In a fourth aspect, the invention provides a fluid for drilling, completing, cementing, stimulating, fracturing, acidizing, or working over a subterranean gas or oil well, or for treating or enhancing the production of oil or gas from an oil or gas bearing formation. The fluid contains between 5 and 99.85 wt % in total of at least one of an organic liquid and water, and between 0.1 and 80 wt % in total of one or more ingredients selected from the group consisting of weighting agents, viscosifiers, dispersants, drilling mud base oils, emulsifiers, soluble salts, cements, proppants, mineral acids, organic acids, biocides, defoamers, demulsifiers, corrosion inhibitors, friction reducers, gas hydrate inhibitors, hydrogen sulfide removal or control additives, asphaltene control additives, paraffin control additives, and scale control additives. The fluid further contains between 0.05 and 10 wt % of one or more compounds according to formula (I) as defined in the third aspect of the invention.

In a fifth aspect, the invention provides a method for drilling, completing, cementing, stimulating, fracturing, acidizing, working over, or treating a subterranean well, including the step of injecting into the well a fluid containing one or more compounds according to formula (I) as defined in the third aspect of the invention.

In a sixth aspect, the invention provides a method for treating a produced stream of oil or gas from an oil and gas bearing formation, including the step of injecting into the produced stream a fluid containing one or more compounds according to formula (I) as defined in the third aspect of the invention.

In a seventh aspect, the invention provides a formulation containing a first component consisting of one or more compounds according to formula (I) as defined in the third aspect of the invention, and a second component. The formulation is fluid at 25° C. The second component consists of one or more materials selected from the group consisting of nonvolatile organic and nonvolatile inorganic materials and mixtures of these. The second component does not include any component of a pre- or post-preparation synthesis reaction mixture for preparation of any of the compounds according to formula (I).

DETAILED DESCRIPTION OF THE INVENTION

The invention relates to novel surfactant compositions that are capable of effectively reducing the dynamic and/or equilibrium surface tension of aqueous systems, and/or affecting foaming performance of such systems. The compositions include 2-hydroxy-3-alkoxypropyl sulfides, sulfones, and sulfoxides according to the following formula (I), wherein Z represents S, SO, and $SO_2$, respectively.

$$R_4OCH_2CH(OH)CR_2R_3ZR_1 \qquad (I)$$

$R_1$ is selected from the group consisting of C3-C16 linear, cyclic, and branched alkyl, alkenyl, aryl, aralkyl, and alkaryl moieties, and any of these moieties substituted with carboxy (—$CO_2H$), sulfo (—$SO_3H$), or phospho (—$PO_3H_2$) substituents; and —$CH_2(CHOH)_nCH_2OH$ (n=0-5).

One way of forming the compounds of formula (I) is by opening the epoxide ring of a glycidyl ether with a thiol (i.e. a mercaptan) of the formula $R_1$—SH, followed (in the case where Z=SO or $SO_2$) by oxidation of the resulting sulfide. Compounds according to formula (I) may also be made by the reaction of glycidyl ethers with mercaptans containing more than one SH group, for example $SH(CH_2)_2O(CH_2)_2SH$, $SH(CH_2)_mSH$ (m =2-4), and $R(O(C_3H_6O)_pCH_2CHOHCH_2SH)_3$ are also included in this invention. One or more of the SH groups may react with a glycidyl ether. Thus $R_1$ may be —$(CH_2)_2O(CH_2)_2T$; —$(CH_2)_mT$; and —$CH_2CH(OH)CH_2(C_3H_6O)_pO$—$R(O(C_3H_6O)_pCH_2CHOHCH_2T)_2$; wherein m is an integer from 2 to 4, p is 1 or 2; T is SH or $ZCR_2R_3CH(OH)CH_2OR_4$, and R is a trimethylolpropane- or glycerol-based segment, provided that Z is not S when $R_1$ is —$CH_2(CHOH)_nCH_2OH$. The term "trimethylolpropane- or glycerol-based segment" refers to a group R that represents either trimethylolpropane or glycerol that has been converted to a tri-ether. The thiol compounds $R_1$—SH described above are all available commercially, or may be made by synthetic techniques known to those of skill in the art. Nonlimiting examples of suitable thiols for use according to the invention include 2-mercaptoethanol, 1-thioglycerol, 1-mercapto-2-propanol, 3-mertapto-1-propanol, 3-mercapto-2-butanol, 4-mercapto-1-butanol, octanethiol, dodecylthiol, ethanedithiol, 1,4-butanedithiol, bis(ethanethiol)ether.

$R_2$ and $R_3$ are each independently selected from the group consisting of H, $CH_3$, linear, and branched alkyl, alkenyl, groups having from one to three carbon atoms.

Each $R_4$ is independently a C3-C30 alkyl, alkenyl, aryl, or aralkyl moiety, and may be branched, linear, or cyclic. It may also be such a moiety bearing a carbonyl group, especially a carboxylic acid, ester, or amide, and/or one or more heteroatoms selected from O, S, and N. Such moieties may be in any location on $R_4$. In some embodiments, $R_4$ is an acyl group. $R_4$ may also be a glycol ether moiety of the formula $R_5(OCH_2CH_2)_q$—, an aminoethylene moiety of the formula $R_5(NHCH_2CH_2)_q$—, or a thioether moiety of the formula $R_5S(CH_2)_q$—, wherein $R_5$ is H or linear C1-C12 alkyl and q is an integer from 1 to 15. The glycol ethers described above are all available commercially, or may be made by synthetic techniques known to those of skill in the art. Thus, although the term "2-hydroxy-3-alkoxypropyl" is used for simplicity to describe the sulfides, sulfones, and sulfoxides of this invention, groups other than alkyl may be used for the $R_4$ group on the ether oxygen at the 3-position of the propyl group. Nonlimiting examples of suitable $R_4$ groups include butyl, hexyl, octyl, 2-ethylhexyl, decyl, dodecyl, tetradecyl, hexadecyl, octadecyl, phenyl, cresyl (any isomer, especially ortho or para, attached at any ring position or at the phenolic oxygen), and mixtures thereof. Typically, the $R_4$ group will be one or more of butyl, 2-ethylhexyl, octyl, decyl, dodecyl, and tetradecyl.

Mixtures of glycidyl ethers may be employed such that the mixture will contain glycidyl ethers having two or more different $R_2$, $R_3$, and/or $R_4$ groups. Examples of suitable glycidyl ethers include, but are not limited to, butyl glycidyl ether, hexyl glycidyl ether, octyl glycidyl ether, nonyl glycidyl ether, decyl glycidyl ether, 2-ethylhexyl glycidyl ether, dodecyl glycidyl ether, tetradecyl glycidyl ether, hexadecyl glycidyl ether, octadecyl glycidyl ether, phenyl glycidyl ether, cresyl glycidyl ether, and the like, and mixtures thereof. More preferred glycidyl ethers are butyl glycidyl ether, 2-ethylhexyl glycidyl ether, C8-C10 glycidyl ethers, and C12-C14 alkyl glycidyl ethers.

Exemplary compositions according to the present invention are 2,3-dihydroxypropyl-2'-hydroxy-3'-(2-ethylhexyloxy)propyl sulfide, 2,3-dihydroxypropyl-2'-hydroxy-3'-dodecyloxypropyl sulfide, 2,3-dihydroxypropyl-2'-hydroxy-3'-hexadecyloxypropyl sulfide, 2,3-dihydroxypropyl-2'-hydroxy-3'-tetradecyloxypropyl sulfide, 2-hydroxyethyl-2'-hydroxy-3'-butoxypropyl sulfide, 2-hydroxyethyl-2'-hydroxy-3'-octyloxypropyl sulfide, 2-hydroxyethyl-2'-hydroxy-3'-nonyloxypropyl sulfide, 2-hydroxyethyl-2'-hydroxy-3'-decyloxypropyl sulfide, 2-hydroxyethyl-2'-hydroxy-3'-dodecyloxypropyl sulfide, 2-hydroxyethyl-2'-hydroxy-3'-hexadecyloxypropyl sulfide, and 2-hydroxyethyl-2'-hydroxy-3'-tetradecyloxypropyl sulfide, 2-hydroxyethyl-2'-hydroxy-3'-(2-ethylhexyloxy)propyl sulfide, 2-dodecyl-2'-hydroxy-3'-butoxypropyl sulfide, and the sulfoxides and sulfones corresponding to any of these.

Preparation of Compounds of Formula (I)

Compounds according to formula (I) may be prepared by any method known in the synthetic organic chemical art. In one exemplary embodiment of the invention, they may be prepared by the reaction of a mercaptan $R_1$—SH with a glycidyl ether according to formula (II), wherein $R_1$, $R_2$, $R_3$, and $R_4$ are as defined above, and wherein Z=S.

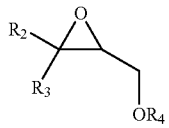
(II)

Compounds wherein Z is SO or $SO_2$ may be made by oxidation of the corresponding compound where Z is S, using any oxidant and oxidation technique known in the art. In one exemplary embodiment of the invention, oxidation is performed with hydrogen peroxide, but other methods may be used.

The amount of glycidyl ether used in the reaction is typically from about 1.0 to about 5 moles per mole of mercaptan, more typically from about 1 to about 4 moles, still more typically from about 1 to about 2 moles, and most typically about 1 mole per mole of mercaptan. Mixtures of glycidyl ethers and/or mixtures of mercaptans may also be employed.

To prepare compounds according to formula (I), the mercaptan may be reacted (adducted) with the glycidyl ether, which may optionally be dispersed in a reaction medium including a diluent, optionally including a catalyst, at a temperature sufficiently high so as to provide a convenient reaction rate and sufficiently low so as to prevent significant by-product formation. By "dispersed," it is meant that the glycidyl ether is suspended in the medium, dissolved in it, or a combination of these. The reaction temperature may be in the range from about 50° C. to about 150° C., preferably from about 50° C. to about 130° C., and more preferably from about 60° C. to about 120° C. The optimum conditions will depend upon the specific reactants, the reactor configuration, the solvents employed, and other variables. A variety of diluents may be used for the reaction, including liquids in which one or more of the reactants is essentially insoluble. More typically, a diluent (if used) will be a material that is a solvent for one or more of the reactants. Examples of suitable solvents include, but are not limited to, isopropanol, ethanol, methanol, acetonitrile, ethylene glycol, propylene glycol, combinations of water and acetonitrile, combinations of water and methanol, combinations of water and isopropanol, combinations of water and ethanol, and mixtures thereof. Typically, isopropanol will be used.

Uses of Compounds of Formula (I)

Compositions according to the invention may also include a variety of other ingredients adapted to complement the utility of compounds of formula (I) in any of a number of applications. The performance properties of such products may be optimized for a specific application by appropriate modification of the structure of the sulfide and the choice of the substituents $R_1$, $R_2$, $R_3$, and $R_4$. Such optimization is routine, and within the ability of the person of ordinary skill in the art in the particular application area. Thus manipulation of these variables yields compounds which may be useful as emulsifiers or detergents, wetting agents, foaming agents, defoamers, rheology modifiers or associative thickeners, dispersants, and the like. As such, these compounds may be useful in applications such as coatings, inks, adhesives, agricultural formulations, fountain solutions, photoresist strippers and developers, shampoos, and detergents and other cleaning compositions. The compounds may also find use in oil-field exploration, development, and production applications such as enhanced oil recovery, fracturing and stimulation processes, and drilling and cementing operations, and may also be useful in various wet-processing textile operations, such as dyeing of fibers and fiber scouring and kier boiling. The general formulation principles governing each of these applications are well known in the respective arts, and a detailed description of the numerous application areas and methods for incorporating the compounds of this invention into such formulations is not necessary to their effective incorporation therein. However, as an indication of the wide scope of possible uses for compounds according to the invention, exemplary but non-limiting formulations are set forth below for a number of application areas.

The terms "water-based", "waterborne", "aqueous", or "aqueous medium", or "aqueous carrier" as used herein refer to systems in which the solvent or liquid dispersing medium comprises at least 50 wt % water, preferably at least 90 wt %, and more preferably at least 95 wt % water. The dispersing medium may consist essentially of water, i.e. it may have no added solvents, or it may also contain solvents.

In broad terms, compounds according to formula (I) may be used in a wide range of formulations that include a second component, such that the application of the second component benefits from the surface active properties provided by the formula (I) material. It is to be understood that, although components of a pre- or post-preparation synthesis reaction mixture for preparation of the compounds according to formula (I) may be present, these do not count as part of the second component for purposes of this invention. Such materials might for example include simple salts, solvents, catalysts, organic precursors, reagents, side products, and byproducts related to the preparation of the compound of formula (I), are not part of the second component. Typically, but not necessarily, the amount by weight of the second component in a formulation will be greater than that of the compound(s) of formula (I).

Formulations containing compounds according to formula (I) according to the invention are typically constructed so as to be fluid at 25° C. They are typically aqueous, but they need not be. The second component may consist of one or more materials selected from nonvolatile organic and nonvolatile inorganic materials, and mixtures of these. As used herein, the term "nonvolatile" means that the indicated material either cannot boil, or it boils at a temperature of at least 150° C. at a pressure of 760 Torr. Thus, although typical low-boiling solvents may be included in the formulation, they do not constitute a part of the second component.

Typical non-limiting examples of nonvolatile materials are given in the exemplary formulations provided hereinafter. Formulations according to the invention may include ready-to-use formulations, or concentrates. Either of these may be further diluted in use. Thus the concentration of the one or more compounds of formula (I) in a composition according to the invention may vary over a wide range. Typically it will be between 0.001 and 45 wt % of the formulation, although in some cases the amount may be as low as 0.00001 wt %. In many cases compositions at the higher end of this concentration range will be diluted during or before use in the intended application, although this is not required in all applications.

By using compounds of formula (I), it is possible to reduce surface tension in a waterborne composition or an industrial process. Thus the invention provides aqueous compositions comprising such compounds, wherein the surfactant provides good wetting properties when used in a surfactant effective amount. For example, the amount of surfactant that is effective to provide enhanced wetting properties of a water-based, organic compound containing composition may range from 0.00001 to 5 wt %, preferably from 0.0001 to 3 wt %, and most preferably from 0.001 to 3 wt %, based on total weight of the formulation. The most favorable amount will vary from one application to another, depending upon the amount and type of other species present in the formulation that are capable of affecting foam properties and wetting performance, for example latex polymers.

A typical water-based coating formulation that includes the surfactants of the invention may include the following components in an aqueous medium, typically at 30 to 80% solids:

| Typical Aqueous-Based coating Formulation | |
|---|---|
| 0 to 50 wt % | Pigment Dispersant/Grind Resin |
| 0 to 80 wt % | Coloring Pigments/Extender Pigments/Anti-Corrosive Pigments/Other Pigment Types |
| 5 to 99.9 wt % | Water-Borne/Water-Dispersible/Water-Soluble Resins |
| 0 to 30 wt % | Slip Additives/Antimicrobials/Processing Aids/Defoamers |
| 0 to 50 wt % | Coalescing or Other Solvents |
| 0.01 to 10 wt % | Surfactant/Wetting/Flow and Leveling Agents, other than Compound of Formula (I) |
| 0.001 to 5 wt % | Compound(s) of Formula (I) |

A typical water-based ink composition that includes the surfactants of the invention may include the following components in an aqueous medium at a 20 to 60% solids content (i.e. not including the coalescing solvent):

| Typical Aqueous-Based Ink Composition | |
|---|---|
| 1-50 wt % | Pigment |
| 0 to 50 wt % | Pigment Dispersant/Grind Resin |
| 0 to 50 wt % | Clay base in appropriate resin solution vehicle |
| 5 to 99.9 wt % | Water-borne/water-dispersible/water-soluble resins |
| 0 to 30 wt % | Coalescing Solvents |
| 0.01 to 10 wt % | Surfactant/Wetting Agents, other than Compound(s) of Formula (I)s |
| 0.01 to 10 wt % | Processing Aids/Defoamers/Solubilizing Agents |
| 0.001 to 5 wt % | Compound(s) of Formula (I) |

A typical water-based agricultural composition that includes the surfactants of the invention may include the following components in an aqueous medium at 0.01 to 80% of the following ingredients:

| Typical Aqueous-Based Agricultural Composition | |
|---|---|
| 0.1-50 wt % | Pesticide or Plant Growth Modifying Agent |
| 0.01 to 10 wt % | Surfactants, other than Compound(s) of Formula (I)s |
| 0 to 5 wt % | Dyes |
| 0 to 20 wt % | Thickeners/Stabilizers/Co-surfactants/Gel Inhibitors/Defoamers |
| 0 to 25 wt % | Antifreeze agent (e.g. ethylene glycol or Propylene glycol) |
| 0.001 to 5 wt % | Compound(s) of Formula (I) |

A typical fountain solution composition for planographic printing that includes the surfactants of the invention may include the following components:

| Typical Fountain Solution for Planographic Printing | |
|---|---|
| 0.05 to 10 wt % | Film forming, water soluble macromolecule |
| 1 to 25 wt % | C2-C12 Alcohol, glycol, or polyol (water soluble, or soluble due to use of a co-solvent) |
| 0.01 to 20 wt % | Water soluble organic acid, inorganic acid, or a salt of these |
| 30 to 98.9 wt % | Water |
| 0.001 to 5 wt % | Compound(s) of Formula (I) |

A typical hard surface cleaner that includes the surfactants of the invention may include the following components:

| Typical Hard Surface Cleaner | |
|---|---|
| 0 to 25 wt % * | Anionic surfactant |
| 0 to 25 wt % * | Cationic surfactant |
| 0 to 25 wt % * | Nonionic surfactant (e.g. alcohol alkoxylates, etc.) |
| 0 to 20 wt % | Chelating agent (EDTA, citrate, tartrate, etc.) |
| 0 to 20 wt % * | Solvent (Glycol ether, lower alcohols, etc.) |
| 0.001 to 25 wt % | Compound(s) of Formula (I) |
| 0 to 2 wt % | Dye, fragrance, preservative, etc. |
| 0 to 40 wt % * | Alkali metal hydroxide |
| Balance to 100 wt % | Water, and optionally other ingredients |

* To total, in combination, between 0.1 and 99 wt %.

A typical water-based photoresist developer or electronic cleaning composition that includes the surfactants of the invention may include the following components:

| Typical Aqueous-Based Photoresist Developer Composition | |
|---|---|
| 0.1 to 3 wt % | Tetramethylammonium hydroxide |
| 0 to 4 wt % | Phenolic resin |
| 92.5 to 99.9 wt % | Water |
| 0.001 to 5 wt % | Compound(s) of Formula (I) |

A typical metalworking fluid that includes the surfactants of the invention may include the following components:

| Typical Synthetic Metalworking Fluid Formulation | |
|---|---|
| 2.5 to 10 wt % | Block copolymer or other emulsifying agent |
| 10 to 25 wt % | Alkanolamine |
| 2 to 10 wt % | Organic monoacid |
| 0 to 5 wt % | Organic diacid |
| 40 to 84.4 wt % | Water |
| 1 to 5 wt % | Biocide |
| 0.001 to 5 wt % | Compound(s) of Formula (I) |

Surfactants are also used in a wide variety of products in the areas of personal care and household and industrial cleaning. The surfactants of the present invention may be used in any of these formulations to provide one or more benefits, with the exact structure of the surfactant compound depending upon the specific performance features required for a particular application. Typical formulations used in these markets are described in Louis Ho Tan Tai's book, *Formulating Detergents and Personal Care Products: A Complete Guide to Product Development* (Champaign, Ill.:

AOCS Press, 2000) as well as in other books, literature, product formularies, etc. familiar to those skilled in the art. A few representative example formulations are described here as illustrations. For example, a rinse aid for use in household automatic dishwashing or in industrial and institutional warewashing may have the ingredients described below.

Typical Rinse Aid Formulation

| | |
|---|---|
| Compound(s) of Formula (I) | 0.001 to 45 wt % |
| Nonionic surfactant other than a compound of Formula (I) (e.g. alkoxylated alcohol(s), alkoxylated block copolymers, etc.) | 0 to 45 wt % |
| Hydrotrope (e.g. sodium xylenesulfonate, sodium toluenesulfonate, anionic surfactant(s), amphoteric surfactant(s), etc.) | 0 to 10 wt % |
| Isopropyl alcohol or ethyl alcohol | 0 to 10 wt % |
| Chelant (e.g. citric acid, etc.) | 5 to 20 wt % |
| Water, and optionally other ingredients | Balance to 100 wt % |

Typical Powdered Laundry Detergent Formulation

| Material | Amount by Weight in Conventional Formulation | Amount by Weight in Concentrated Formulation |
|---|---|---|
| Compound(s) of Formula (I) | 0.001 to 5 wt % | 0.001 to 15 wt % |
| Detergent surfactant(s) (e.g. anionic surfactants, alcohol alkoxylates, etc.) | 0.1 to 30 wt % | 0.1 to 50 wt % |
| Builder/co-builder (zeolites, sodium carbonate, phosphates, etc.) | 25 to 50 wt % | 25 to 60 wt % |
| Bleach and bleach activator (perborates, etc.) | 0 to 25 wt % | 0 to 25 wt % |
| Other Additives (fragrance, enzymes, hydrotropes, etc.) | 0 to 7 wt % | 1 to 10 wt % |
| Fillers (sodium sulfate, etc.) | 5 to 35 wt % | 0 to 12 wt % |

Typical Aqueous Liquid Laundry Detergent Formulation

| Material | Amount by Weight in Conventional Formulation | Amount by Weight in Concentrated Formulation |
|---|---|---|
| Compound(s) of Formula (I) | 0.001 to 25 wt % | 0.001 to 30 wt % |
| Detergent surfactant(s) (e.g. anionic surfactants, alcohol alkoxylates, etc.) | 0 to 35 wt % | 0 to 65 wt % |
| Builder/co-builder (citrate, tartrate, etc.) | 3 to 30 wt % | 0 to 36 wt % |
| Other Additives (fragrances, dyes, etc.) | 0.1 to 5 wt % | 1 to 5 wt % |
| Water and other solvents (e.g. lower alcohols) | 5 to 75 wt % | 1 to 56 wt % |

Typical Non-Aqueous Laundry Detergent Formulation

| Material | Amount by Weight |
|---|---|
| Compound(s) of Formula (I) | 0.001 to 30 wt % |
| Detergent surfactant(s) (e.g. anionic surfactants, alcohol alkoxylates, amine oxides, etc.) | 0.1 to 42 wt % |
| Builder/co-builder (zeolites, sodium carbonate, phosphates, citrate or tartrate salts, etc.) | 25 to 60 wt % |
| Bleach and bleach activator (perborates, etc.) | 0 to 20 wt % |
| Anti-redeposition aids (sodium carboxymethylcellulose, etc.) | 0.5 to 5 wt % |
| Other Additives (fragrance, enzymes, etc.) | 0 to 5 wt % |
| Polyalkylene glycol | 0 to 50 wt % |

Typical 2-Part Industrial and Institutional Laundry Formulation

| | Amount by Weight of Material in Each Pack |
|---|---|
| Pack A | |
| Compound(s) of Formula (I) | 0.001 to 20 wt % |
| Detergent surfactant(s) (e.g. anionic surfactants, alcohol alkoxylates, etc.) | 0 to 20 wt % |
| Antiredeposition aids (sodium carboxymethylcellulose, etc.) | 0.01 to 2 wt % |
| Water, and optionally other ingredients | Balance to 100 wt % |
| Pack B | |
| Sodium silicate | 5 to 10 wt % |
| Sodium metasilicate | 0 to 30 wt % |
| Tetrapotassium pyrophosphate | 0 to 10 wt % |
| potassium hydroxide | 0 to 35 wt % |
| potassium carbonate | 0 to 15 wt % |
| Water, and optionally other ingredients | Balance to 100 wt % |
| Mix Ratio Pack A:Pack B | 1:2 to 1:4 |

Typical Shampoo or Liquid Body Wash Formulation

| Material | Amount by Weight |
|---|---|
| Compound(s) of Formula (I) | 0.001 to 5 wt % |
| Anionic surfactant(s) (e.g. sodium or ammonium lauryl sulfate, sodium or ammonium lauryl sulfate, etc.) | 0.1 to 30 wt % |
| Amphoteric cosurfactant(s) (e.g. cocoamidopropyl betaine, etc.) | 0 to 20 wt % |
| Nonionic surfactant other than a compound of Formula (I) (e.g. alcohol alkoxylates, sorbitan esters, alkyl glucosides, etc.) | 0 to 20 wt % |
| Cationic polymers (e.g. polyquaternium, etc.) | 0 to 5 wt % |
| Other Additives (fragrance, dyes, oils, opacifiers, preservatives, chelants, hydrotropes, etc.) | 0 to 15 wt % |
| Polymeric thickeners (e.g. polyacrylate, etc.) | 0 to 2 wt % |
| Conditioning oils (e.g. sunflower oil, petrolatum, etc.) | 0 to 10 wt % |
| Citric acid | 0 to 2 wt % |
| Ammonium chloride or sodium chloride | 0 to 3 wt % |
| Humectants (e.g. propylene glycol, glycerin, etc.) | 0 to 15 wt % |
| Glycol distearate | 0 to 5 wt % |
| Cocoamide (i.e. cocoamide MEA, cocoamide MIPA, PEG-5 cocoamide, etc.) | 0 to 10 wt % |
| Dimethicone | 0 to 5 wt % |
| Behenyl alcohol | 0 to 5 wt % |
| Water, and optionally other ingredients | Balance to 100 wt % |

| Typical Hair Conditioner Formulation | |
| --- | --- |
| Material | Amount by Weight |
| Compound(s) of Formula (I) | 0.001 to 10 wt % |
| Nonionic surfactant other than a compound of Formula (I), and/or fatty alcohol(s) (e.g. stearyl alcohol, etc.) | 0.1 to 10 wt % |
| Cationic surfactant(s) (e.g. cetrimonium chloride, etc.) | 0 to 10 wt % |
| Anionic surfactants (e.g. TEA-dodecylbenzenesulfonate, etc.) | 0 to 5 wt % |
| Silicones (e.g. dimethicone, dimethiconal, etc.) | 0 to 5 wt % |
| Cationic polymers (e.g. polyquaternium, etc.) | 0 to 10 wt % |
| Other Additives (fragrance, dyes, oils, opacifiers, preservatives, chelants, hydrotropes, etc.) | 0 to 10 wt % |
| Thickening polymers (e.g. hydroxyethylcellulose, polyacrylates, etc.) | 0 to 5 wt % |
| Potassium, ammonium or sodium chloride | 0 to 5 wt % |
| Humectant (e.g. propylene glycol, etc.) | 0 to 5 wt % |
| Panthenol | 0 to 2 wt % |
| Water, and optionally other ingredients | Balance to 100 wt % |

| Typical Aqueous Sunscreen Formulation | |
| --- | --- |
| Material | Amount by Weight |
| Compound(s) of Formula (I) | 0.001 to 30 wt % |
| Polyethylene glycol (e.g. PEG-8, etc.) | 0 to 30 wt % |
| Active sunscreen agents (e.g. octyl methoxycinnamate, azobenzone, homosalate, octyl salicylate, oxybenzone, octocrylene, butyl methoxydibenzoylmethane, octyl triazone, etc.) | 1 to 30 wt % |
| Esters and emollients (e.g. dimethicone, methylparaben, propylparaben, polysorbates, etc.) | 0 to 20 wt % |
| Thickening polymers (e.g. acrylates/C10-30 alkyl acrylate crosspolymer, PVP/hexadecene copolymer, etc.) | 0 to 20 wt % |
| Other Additives (fragrance, dyes, oils, opacifiers, preservatives, chelants, etc.) | 0 to 15 wt % |
| Solvent/hydrotropes (e.g. propylene glycol, benzyl alcohol, dicapryl ether, etc.) | 0 to 20 wt % |
| Triethanolamine | 0 to 5 wt % |
| Water, and optionally other ingredients | Balance to 100 wt % |

Cement Admixture Formulations

Cement admixtures may be of any of several types, including superplasticizing, plasticizing, accelerating, set retarding, air entraining, water-resisting, corrosion inhibiting, and other types. Such admixtures are used to control the workability, settling and end properties (strength, impermeability, durability and frost/deicing salt resistance, etc.) of cementitious products like concretes, mortars, etc. The admixtures are usually provided as aqueous solutions and they can be added to the cementitious system at some point during its formulation. Surfactants of this invention may provide wetting, foam control, flow and leveling, water reduction, corrosion inhibition, high ionic strength tolerance and compatibility, and other benefits when used in such systems.

| Exemplary Cement Admixture Ingredients | |
| --- | --- |
| Material | Amount by Weight Relative to Cement Weight |
| Compound(s) of Formula (I) | 0.001 to 5 wt % |
| Solubilizing agents (solvent, hydrotropes, amines, etc.) * | 0 to 10 wt % |
| Polymers and/or oligomers (e.g. lignosulfonates, sulfonated melamine formaldehyde condensates, polycarboxylates, styrene-maleic anhydride oligomers, copolymers and their derivatives, etc.) * | 0 to 5 wt % |
| Functional Additives (defoamers, air entraining or detraining agents, pH control additives, corrosion inhibitors, set retarders, accelerators, preservatives, etc.) * | 0 to 5 wt % |
| Water | 40 to 75% |

* To total, in combination, between 0.1 and 20 wt %.

Oil and Gas Field Formulations

Surfactants of this invention, used alone or as a component in formulations, may provide surface tension reduction, foam control, and improved wetting in a variety of applications within the Oil and Gas industry. These may include, for example, formulations for the following uses.

In drilling applications, the surfactants may be used in formulations for dispersion of clays and drill cuttings, ROP (rate of penetration) enhancement, emulsification and de-emulsification, surface wetting and surface tension reduction, shale stabilization, and enhancement of hydration or dissolution of solid additives.

In cementing, stimulation and workover applications, uses may include formulations for spacers, cement dispersion, de-air entraining and defoaming, cement retardation, fracturing fluids, stimulation of coal bed methane, surface or interfacial tension reduction, oil/water wetting, and cleaning fluids.

In oil and gas production, uses may include rig wash formulations, defoaming of crude, water flooding/injection, defoaming for acid gas sweetening, oil/water separation, enhanced oil recovery, and inhibition or dispersion of asphaltenes, hydrates, scale and waxes.

Exemplary fluids for drilling, completing, cementing, stimulating, fracturing, acidizing, or working over of subterranean wells, or for enhancing production from an oil- or gas-bearing formation or treating the produced oil or gas, typically include from 0.05 to 10 wt % of a surfactant of this invention in a fluid containing water and/or an organic liquid, which typically constitutes from 5 to 99.85 wt % of the fluid. The organic liquid is typically a petroleum product, although it need not be, and may for example include crude oil or any of the drilling mud base oils described below. If water is included, it may be from a freshwater, sea water, or brine source, or it may be provided by inclusion of an aqueous mineral acid such as hydrochloric acid, hydrofluoric acid, sulfuric acid, etc. Fluids for such applications usually also include between 0.1 and 80 wt % in total of one or more ingredients selected from weighting agents, viscosifiers, dispersants, drilling mud base oils, emulsifiers, soluble salts, cements, proppants, mineral acids, organic acids, biocides, defoamers, demulsifiers, corrosion inhibitors, friction reducers, gas hydrate inhibitors, hydrogen sulfide removal or control additives, asphaltene control additives, paraffin control additives, and scale control additives. A variety of specific materials are known in the art for performing these functions. Suitable nonlimiting examples of some of these materials follow, and others will be apparent to those of skill in the art.

Weighting agents: barium sulfate, hematite, and ilmenite.

Viscosifiers: clays (e.g. bentonite, attapulgite), water-soluble polymers (e.g. xanthan gum, guar, polysaccharides, modified polysaccharides), organophilic clays, and oil-soluble polymers.

Dispersants: lignosulfonates, naphthalene sulfonates, sulfonated melamine formaldehyde resins.

Drilling mud base oils: diesel, mineral oil, olefinic oils, paraffinic oils, and esters.

Emulsifiers: fatty acids, fatty amides, anionic surfactants, and nonionic alkoxylated surfactants.

Soluble salts (e.g. for specific gravity adjustment, shale stabilization, or osmotic pressure control): NaCl, NaBr, KCl, KBr, $CaCl_2$, $CaBr_2$, $ZnCl_2$, $ZnBr_2$, sodium formate, potassium formate, and cesium formate.

Cements

Other Surfactants: cationic surfactants, amphoteric surfactants, alkyl glucosides, phosphate esters, and fluorosurfactants.

Proppants: ceramics, sintered bauxite, sand, and resin-coated sand.

Organic Acids: formic acid, acetic acid, citric acid.

Mineral acids: hydrochloric acid and hydrofluoric acid.

The foregoing classes of materials may find application, when used in combination with the surfactants of this invention, in a variety of oilfield applications. Depending upon the exact application and desired effect, compositions may be injected into a well or added to the stream of oil or gas produced by the well, all according to methods well known in the art.

Typical applications, and the ingredients commonly (although not necessarily) used in making formulations for these purposes, are shown immediately below. Other ingredients may also be present. It will be understood that each of these formulations will also contain a surfactant according to the invention.

Water-based drilling muds: weighting agents, viscosifiers, and dispersants.

Oil-based drilling muds: base oil, emulsifier, and viscosifier.

Completion fluids: soluble salts for specific gravity adjustment.

Cement Formulations: the cements themselves, in combination with dispersants.

Spacers: weighting agents and surfactants.

Acidizing fluids: surfactants and one or both of mineral acids and organic acids.

Fracturing fluids: viscosifiers, proppants, and surfactants.

Fluids for stimulating or enhancing production from a gas or oil bearing formation, may contain ingredients similar to those found in fracturing fluids, except for proppants. Finally, fluids for treating oil or gas produced in the above ways may include one or more of biocides, defoamers, demulsifiers, corrosion inhibitors, friction reducers, gas hydrate inhibitors, hydrogen sulfide removal or control additives, asphaltene control additives, paraffin control additives, and scale control additives.

As will be appreciated in light of the foregoing discussion, the surfactants of this invention may find utility in a wide variety of applications. The present invention is further illustrated by the following examples, which are presented for purposes of demonstrating, but not limiting, the methods and compositions of this invention.

EXAMPLES

Example 1

Reaction of 1-thioglycerol with 2-ethylhexyl glycidyl ether

A solution of 2-ethylhexyl glycidyl ether (9.04 g, 48.53 mmol) in isopropanol (10 mL) was treated with 1-thioglycerol (5 g, 46.22 mmol) under nitrogen in a 100 mL 3-neck round bottom flask equipped with a $N_2$ inlet, a rubber septum, glass stopper and a magnetic stir bar. The mixture was heated at 90° C. and monitored for completion by gas chromatography/mass spectrometry (g.c.m.s.) for disappearance of starting materials and formation of the product. After 3 h, the reaction was judged to be complete. The mixture was cooled to ambient temperature and the solvent was distilled in-vacuo to afford the product. The product, 2,3-dihydroxypropyl-2'-hydroxy-3'-(2-ethylhexyloxy)propyl sulfide, was identified by mass spectrometry as well as $^1H$ and $^{13}C$ NMR.

Example 2

Reaction of 1-thioglycerol with C12-C16 glycidyl ethers

This reaction was carried out in a similar manner to that described in Example 1, starting with 1-thioglycerol (5 g, 46.22 mmol) and the glycidyl ethers mixture (12.3 g, ~50.84 mmol). The product, a mixture of 2,3-dihydroxypropyl-2'-hydroxy-3'-dodecyloxypropyl sulfide, 2,3-dihydroxypropyl-2'-hydroxy-3'-tetradecyloxypropyl sulfide and 2,3-dihydroxypropyl-2'-hydroxy-3'-hexadecyloxypropyl sulfide, was identified as in Example 1.

Example 3

Reaction of 2-mercaptoethanol with butyl glycidyl ether

This reaction was carried out in a similar manner to that described in Example 1, starting with 2-mercaptoethanol (2.0 g, 26.6 mmol) and butyl glycidyl ether (3.50 g, 26.88 mmol) in 5 mL of isopropanol. The product, 2-hydroxyethyl-2'-hydroxy-3'-butoxypropyl sulfide, was identified as in Example 1.

Example 4

Reaction of 2-mercaptoethanol with C12-C16 glycidyl ethers mixture

This reaction was carried out in a similar manner to that described in Example 1, starting with 2-mercaptoethanol (2.0 g, 26.6 mmol) and a C12-C16 glycidyl ethers mixture (6.50 g, ~26.88 mmol) in 5 mL of isopropanol. The product was a mixture of 2-hydroxyethyl-2'-hydroxy-3'-dodecyloxypropyl sulfide, 2-hydroxyethyl-2'-hydroxy-3'-tetradecyloxypropyl sulfide, and 2-hydroxyethyl-2'-hydroxy-3'-hexadecyloxypropyl sulfide, identified as in Example 1.

Example 5

Reaction of 2-mercaptoethanol with 2-ethylhexyl glycidyl ether

This reaction was carried out in a similar manner to that described in Example 1, starting with 2-mercaptoethanol (2.0 g, 26.6 mmol) and 2-ethylhexyl glycidyl ether (5.03 g, 26.88 mmol) in 5 mL of isopropanol. The product, 2-hydroxyethyl-2'-hydroxy-3'-(2-ethylhexyloxy)propyl sulfide, was identified as in Example 1.

Example 6

Reaction of 2-mercaptoethanol with C8-C10 glycidyl ether mixture

This reaction was carried out in a similar manner to that described in Example 1, starting with 2-mercaptoethanol (985 g, 12.61 mol) and a C8-C10 glycidyl ethers mixture (1200 g, ~6.45 mol) in 1000 mL of isopropanol. The product was a mixture of 2-hydroxyethyl-2'-hydroxy-3'-octyloxypropyl sulfide and 2-hydroxyethyl-2'-hydroxy-3'-decyloxypropylsulfide, identified as in Example 1.

Example 7

Preparation of the sulfoxide and sulfone derivative of 2-hydroxyethyl-2'-hydroxy-3'-dodecylpropyl sulfide A solution of the sulfide (5.0 g, 15.06 mmol) in isopropanol (20 mL) is treated with a 30% solution of $H_2O_2$ in water (6.83 mL, 60.24 mmol) under nitrogen in a 100-mL 3-neck round bottom flask equipped with an $N_2$ inlet, a rubber septum, a glass stopper and a magnetic stir bar. The mixture is heated at 60° C. for 24 h, cooled to ambient temperature, treated with an aqueous saturated $NaHSO_3$ solution (5.0 mL), and extracted into ethyl acetate (50 mL). The organic phase is dried over $MgSO_4$, filtered, and evaporated in-vacuo to give the product as an approximately 1:1 mixture of 2-hydroxyethyl-2'-hydroxy-3'-dodecyloxypropyl sulfoxide and 2-hydroxyethyl-2'-hydroxy-3'-dodecyloxypropyl sulfone.

The reactants and products of Examples 1-6 are shown in Table 1 below.

TABLE 1

TABLE 1-continued

Thiol/Glycidyl Ether Adducts

| Example | Thiol | Glycidyl Ether | Product |
|---|---|---|---|
| 5 |  | 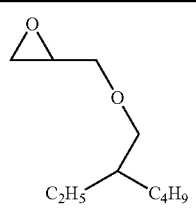 | 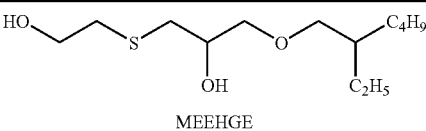<br>MEEHGE |
| 6 |  | 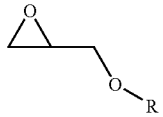<br>R = mix of $C_8H_{17}$, $C_{10}H_{21}$ | 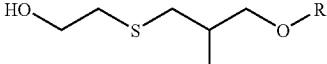<br>MEODGE<br>R = mix of $C_8H_{17}$, $C_{10}H_{21}$ |

Examples 8-13

Equilibrium Surface Tensions

Equilibrium surface tensions were determined for the compounds prepared in Examples 1-6, using a Kruss K-12 tensiometer with a platinum Wilhelmy plate, maintaining the temperature at 25±1° C. by means of a constant temperature circulating bath. The results, reported in Table 2, are averages of 10 measurements over a 10-minute period, and have a standard deviation of less than 0.01 dyne/cm.

TABLE 2

Equilibrium Surface Tension Data for Thiol/Glycidyl Ether Adducts

| Example | Adduct | Equilibrium Surface Tension (dynes/cm) | | Water Solubility |
|---|---|---|---|---|
| | | 0.1 wt % | 1.0 wt % | |
| #8 | TGEHGE | 28.3 | 26.7 | <0.1 wt % |
| #9 | TGDDGE | 27.6 | 26.8 | <0.1 wt % |
| #10 | MEBGE | 37.1 | 32.6 | <0.1 wt % |
| #11 | MEDDGE | 27.4 | 27.5 | <0.1 wt % |
| #12 | MEEHGE | 30.7 | 29.3 | <0.1 wt % |
| #13 | MEODGE | 27.5 | 27.5 | <0.1 wt % |

Examples 14-19

Foam Characteristics of Thiol/Glycidyl Ether Adducts

Foam height and stability (time to reach zero foam) were measured by the Ross-Miles foam test, using 0.1 wt % solutions of the surfactants. The results of these determinations are presented in Table 3.

TABLE 3

Foam Stability Data

| Example | Compound | Initial Foam Height (cm) | Final Foam Height (cm) at 300 Sec | Time to 0 foam (sec) |
|---|---|---|---|---|
| 14 | TGEHGE | 1.0 | 0 | 6 |
| 15 | TGDDGE | 2.3 | 2.3 | >300 |
| 16 | MEBGE | 1.2 | 0 | 2 |
| 17 | MEDDGE | 0.5 | 0 | 3 |
| 18 | MEEHGE | 0.6 | 0 | 6 |
| 19 | MEODGE | 1.6 | 0 | 0 |

The data in Table 3 demonstrate that a range of foam performance may be obtained, depending upon the glycidyl ether capping group. While applications such as coatings, inks, and adhesives require low foam or foam that dissipates quickly, other applications such as cleaning or ore floatation require a controlled amount of foam to be present and to persist. Therefore, compositions incorporating compounds according to formula (I) may find utility in a wide range of applications.

Examples 20-25

Dynamic Surface Tension Data

Dynamic surface tensions were determined for the compounds prepared in Examples 1-5, at 0.1 and 1.0 wt % levels, using a Kruss BP-2 Bubble Pressure Tensiometer. The results of these determinations are shown in Table 4.

TABLE 4

Dynamic surface tension data

| Example | Compound | Dynamic surface tension (dynes/cm, 0.1 wt %) | | | Dynamic surface tension (dynes/cm, 1.0 wt %) | | |
|---|---|---|---|---|---|---|---|
| | | 1 b/s | 5 b/s | 20 b/s | 1 b/s | 5 b/s | 20 b/s |
| #20 | TGEHGE | 37 | 47 | 53 | 27 | 28 | 30 |
| #21 | TGDDGE | 42 | 70 | 70 | 27 | 57 | 70 |

TABLE 4-continued

Dynamic surface tension data

| | | Dynamic surface tension (dynes/cm, 0.1 wt %) | | | Dynamic surface tension (dynes/cm, 1.0 wt %) | | |
|---|---|---|---|---|---|---|---|
| Example | Compound | 1 b/s | 5 b/s | 20 b/s | 1 b/s | 5 b/s | 20 b/s |
| #22 | MEBGE | 59 | 61 | 65 | 43 | 44 | 44 |
| #23 | MEDDGE | 72 | 72 | 72 | 30 | 33 | 57 |
| #24 | MEEHGE | 35 | 39 | 45 | 30 | 30 | 32 |
| #25 | MEODGE | 29 | 35 | 43 | 28 | 29 | 30 | b/s = bubbles/second

The data in Table 4 show that a wide range of dynamic surface tension reduction is possible with this family of molecules providing differing surfactants for strong (Examples 20, 24), moderate (Examples 22, 23), or low (Example 21) surface tension reduction of an aqueous solution or formulation. Depending upon the mode of application of a formulation and the substrate to be wetted (brush application of an industrial coating, spray application of an industrial cleaner, roller application of an adhesive), surfactants that provide such a wide range of dynamic surface tension reduction may find significant commercial utility.

This invention provides novel surfactants with properties that make suitable for use in a wide range of industrial and commercial applications. Such applications include water-based coatings, inks, adhesives, agricultural formulations, aqueous and non-aqueous cleaning compositions, personal care applications, and formulations for textile processing and oilfield applications.

Although the invention is illustrated and described herein with reference to specific embodiments, it is not intended that the subjoined claims be limited to the details shown. Rather, it is expected that various modifications may be made in these details by those skilled in the art, which modifications may still be within the spirit and scope of the claimed subject matter and it is intended that these claims be construed accordingly.

What is claimed:

1. In a formulation that is fluid at 25° C. comprising between 0.1 and 99.9 wt % in total of one or more ingredients selected from the group consisting of surfactants and wetting agents other than according to formula (I); alkali metal hydroxides; water-borne, water-dispersible, or water-soluble resins; flow agents; leveling agents; pigments; processing aids; defoamers; solubilizing agents; pesticides; plant growth modifying agents; water-soluble film-forming macromolecules; polyols; water-soluble acids or salts thereof; tetramethylammonium hydroxide; emulsifying agents; alkanolamines; organic monoacids; biocides; chelants; detergent builders; detergent co-builders; dyes; fragrances; anti-redeposition aids; sunscreen agents; polymers; oligomers; functional cement additives; sodium chloride; sodium bromide; calcium chloride; calcium bromide; zinc chloride; zinc bromide; cesium formate; hydrochloric acid; hydrofluoric acid; acetic acid; and formic acid;

the improvement comprising including in the formulation between 0.001 and 45 wt % of one or more compounds according to formula (I)

$$R_4OCH_2CH(OH)CR_2R_3ZR_1 \qquad (I)$$

wherein $R_4$ is selected from the group consisting of C3-C30 branched, linear, and cyclic alkyl, alkenyl, aryl, and aralkyl moieties;

$R_2$ and $R_3$ are each independently selected from the group consisting of H and linear or branched C1-C3 alkyl and C2-C3 alkenyl groups;

$R_1$ is -CH$_2$(CHOH)$_n$CH$_2$OH wherein n is 0 or 1; and Z is S, SO, or SO$_2$; and wherein said one or more ingredients does not include any component of a pre- or post-preparation synthesis reaction mixture for preparation of any of the one or more compounds according to formula (I).

2. The formulation of claim 1, wherein the formulation is a hard surface cleaning formulation comprising water and between 0.1 and 99 wt % in total of one or more ingredients selected from the group consisting of anionic surfactants, cationic surfactants, nonionic surfactants other than according to formula (I), solvents, and alkali metal hydroxides, the formulation comprising between 0.001 and 25 wt % of one or more compounds of formula (I).

3. The formulation of claim 1, wherein the formulation is a coating formulation comprising between 5 and 99.9 wt % of a water-borne, water-dispersible, or water-soluble resin, and between 0.01 and 10 wt % in total of one or more other additives selected from the group consisting of surfactants, wetting agents, and flow and leveling agents, other than according to formula (I), the formulation comprising between 0.001 and 5 wt % of one or more compounds of formula (I).

4. The formulation of claim 1, wherein the formulation is an ink formulation comprising between 1 and 50 wt % of a pigment, between 5 and 99.9 wt % of a water-borne, water-dispersible, or water-soluble resin, between 0.01 and 10 wt % of a surfactant or wetting agent other than according to formula (I), and between 0.01 and 10 wt % in total of one or more other additives selected from the group consisting of processing aids, defoamers, and solubilizing agents, the formulation comprising between 0.001 and 5 wt % of one or more compounds of formula (I).

5. An agricultural formulation comprising between 0.1 and 50 wt % of a pesticide or plant growth modifying agent and between 0.01 and 10 wt % of a surfactant or wetting agent other than according to formula (I), the formulation comprising between 0.001 and 5 wt % of one or more compounds of formula (I)

$$R_4OCH_2CH(OH)CR_2R_3ZR_1 \qquad (I)$$

wherein $R_4$ is selected from the group consisting of C3-C30 branched, linear, and cyclic alkyl, alkenyl, aryl, and aralkyl moieties;

$R_2$ and $R_3$ are each independently selected from the group consisting of H and linear or branched C1-C3 alkyl and C2-C3 alkenyl groups;

$R_1$ is -CH$_2$(CHOH)$_n$CH$_2$OH wherein n is 0 or 1; and Z is S, SO, or SO$_2$.

6. The formulation of claim 1, wherein the formulation is a fountain solution formulation for planographic printing comprising between 0.05 and 10 wt % of a water-soluble, film forming macromolecule, between 1 and 25 wt % of a water-soluble alcohol, glycol, or polyol, between 0.01 and 20 wt % of a water-soluble acid or its salt, and between 30 and 98.9 wt % of water, the formulation comprising between 0.001 and 5 wt % of one or more compounds of formula (I).

7. The formulation of claim 1, wherein the formulation is a photoresist developer formulation comprising between 0.1 and 3 wt % of tetramethylammonium hydroxide and between 92.5 and 99.9 wt % of water, the formulation comprising between 0.001 and 5 wt % of one or more compounds of formula (I).

8. The formulation of claim 1, wherein the formulation is a synthetic metalworking fluid formulation comprising between 2.5 and 10 wt % of an emulsifying agent, between 10 and 25 wt % of an alkanolamine, between 2 and 10 wt % of an organic monoacid, between 1 and 5 wt % of a biocide, and between 40 and 84.4 wt % of water, the formulation comprising between 0.001 and 5 wt % of one or more compounds of formula (I).

9. The formulation of claim 1, wherein the formulation is a rinse aid formulation comprising water and between 5 and 20 wt % of a chelant, the formulation comprising between 0.001 and 45 wt % of one or more compounds of formula (I).

10. A powdered laundry detergent formulation comprising between 0.1 and 50 wt % of one or more detergent surfactants and between 25 and 60 wt % of a builder or co-builder, the formulation further comprising between 0.001 and 15 wt % of one or more compounds of formula (I)

R$_4$OCH$_2$CH(OH)CR$_2$R$_3$ZR$_1$    (I)

wherein R$_4$ is selected from the group consisting of C3-C30 branched, linear, and cyclic alkyl, alkenyl, aryl, and aralkyl moieties;

R$_2$ and R$_3$ are each independently selected from the group consisting of H and linear or branched C1-C3 alkyl and C2-C3 alkenyl groups;

R$_1$ is -CH$_2$(CHOH)$_n$CH$_2$OH wherein n is 0 or 1; and Z is S, SO, or SO$_2$.

11. The formulation of claim 1, wherein the formulation is an aqueous liquid laundry detergent formulation comprising between 0.1 and 65 wt % of one or more detergent surfactants, between 3 and 36 wt % of a builder or co-builder, between 0.1 and 5 wt % in total of one or more other additives selected from the group consisting of fragrances and dyes, and between 1 and 75 wt % in total of one or more other additives selected from the group consisting of water and other solvents, the formulation comprising between 0.001 and 30 wt % of one or more compounds of formula (I).

12. A non-aqueous laundry detergent formulation comprising between 0.1 and 42 wt % of one or more detergent surfactants, between 25 and 60 wt % of a builder or co-builder, and between 0.5 and 5 wt % of an anti-redeposition aid, the formulation comprising between 0.001 and 30 wt % of one or more compounds of formula (I)

R$_4$OCH$_2$CH(OH)CR$_2$R$_3$ZR$_1$    (I)

wherein R$_4$ is selected from the group consisting of C3-C30 branched, linear, and cyclic alkyl, alkenyl, aryl, and aralkyl moieties;

R$_2$ and R$_3$ are each independently selected from the group consisting of H and linear or branched C1-C3 alkyl and C2-C3 alkenyl groups;

R$_1$ is -CH$_2$(CHOH)$_n$CH$_2$OH wherein n is 0 or 1; and Z is S, SO, or SO$_2$.

13. The formulation of claim 1, wherein the formulation is an industrial and institutional laundry detergent formulation comprising water and between 0.01 and 2 wt % of an anti-redeposition aid, the formulation comprising between 0.001 and 20 wt % of one or more compounds of formula (I).

14. The formulation of claim 1, wherein the formulation is a shampoo or liquid body wash formulation comprising water and between 0.1 and 30 wt % of an anionic surfactant, the formulation comprising between 0.001 and 5 wt % of one or more compounds of formula (I).

15. The formulation of claim 1, wherein the formulation is a hair conditioner formulation comprising water and between 0.1 and 10 wt % of a nonionic surfactant other than according to formula (I), the formulation comprising between 0.001 and 10 wt % of one or more compounds of formula (I).

16. The formulation of claim 1, wherein the formulation is an aqueous sunscreen formulation comprising water and between 1 and 30 wt % of a sunscreen agent, the formulation comprising between 0.00 1 and 30 wt % of one or more compounds of formula (I).

17. The formulation of claim 1, wherein the formulation is a cement admixture formulation comprising between 40 and 75 wt % of water and between 0.1 and 20 wt % in total of one or more solubilizing agents, polymers, oligomers, or functional additives, the formulation comprising between 0.001 and 5 wt % of one or more compounds of formula (I).

18. The formulation of claim 1, wherein R$_4$ is selected from the group consisting of butyl, 2-ethylhexyl, octyl, decyl, dodecyl, tetradecyl, and mixtures of any of these; and R$_2$ and R$_3$ are both H.

19. The formulation of claim 18, wherein Z is S.

20. In a fluid for drilling, completing, cementing, stimulating, fracturing, acidizing, or working over a subterranean gas or oil well, or for treating or enhancing the production of oil or gas from an oil or gas bearing formation; the fluid comprising between 5 and 99.85 wt % in total of at least one of an organic liquid and water and further comprising between 0.1 and 80 wt % in total of one or more ingredients selected from the group consisting of weighting agents, viscosifiers, dispersants, drilling mud base oils, emulsifiers, soluble salts, cements, proppants, mineral acids, organic acids, biocides, defoamers, demulsifiers, corrosion inhibitors, friction reducers, gas hydrate inhibitors, hydrogen sulfide removal or control additives, asphaltene control additives, paraffin control additives, and scale control additives;

the improvement comprising including in the fluid between 0.05 and 10 wt % of one or more compounds according to formula (I)

R$_4$OCH$_2$CH(OH)CR$_2$R$_3$ZR$_1$    (I)

wherein R$_4$ is selected from the group consisting of C3-C30 branched, linear, and cyclic alkyl, alkenyl, aryl, and aralkyl moieties;

R$_2$ and R$_3$ are each independently selected from the group consisting of H and linear or branched C1-C3 alkyl and C2-C3 alkenyl groups;

R$_1$ is -CH$_2$(CHOH)$_n$CH$_2$OH wherein n is 0 or 1; and Z is S, SO, or SO$_2$; and wherein said one or more ingredients does not include any component of a pre- or post-preparation synthesis reaction mixture for preparation of any of the one or more compounds according to formula (I).

21. A formulation comprising:

i) a first component consisting of one or more compounds according to formula (I)

R$_4$OCH$_2$CH(OH)CR$_2$R$_3$ZR$_1$    (I)

wherein R$_4$ is selected from the group consisting of C3-C30 branched, linear, and cyclic alkyl, alkenyl, aryl, and aralkyl moieties;

R$_2$ and R$_3$ are each independently selected from the group consisting of H and linear or branched C1-C3 alkyl and C2-C3 alkenyl groups; and R$_1$ is -CH$_2$(CHOH)$_n$CH$_2$OH wherein n is 0 or 1; and Z is S, SO, or SO$_2$; and ii) a second component consisting of one or more materials selected from the group consisting of nonvolatile organic and nonvolatile inorganic materials and mix-

tures of these, said second component not including any component of a pre- or post-preparation synthesis reaction mixture for preparation of any of the one or more compounds according to formula (I);
wherein the formulation is fluid at 25° C.

22. The formulation of claim 21, wherein the second component is present in a greater amount by weight than the first component.

23. The formulation of claim 22, wherein the formulation comprises an aqueous carrier.

24. The formulation of claim 21, wherein the second component consists of one or more materials selected from the group consisting of surfactants or wetting agents other than according to formula (I); solvents; alkali metal hydroxides; water-borne, water-dispersible, or water-soluble resins; flow agents; leveling agents; pigments; processing aids; defoamers; solubilizing agents; pesticides; plant growth modifying agents; water-soluble film-forming macromolecules; water-soluble alcohols, glycols, or polyols; water-soluble acids or salts thereof; tetramethylammonium hydroxide; emulsifying agents; alkanolamines; organic monoacids; biocides; chelants; detergent builders; detergent co-builders; dyes; fragrances; anti-redeposition aids; sunscreen agents; solubilizing agents; polymers; oligomers; and functional cement additives.

25. The formulation of claim 21, wherein $R_4$ is selected from the group consisting of butyl, 2-ethylhexyl, octyl, decyl, dodecyl, tetradecyl, and mixtures of any of these; and $R_2$ and $R_3$ are both H.

26. The formulation of claim 25, wherein Z is S.

27. The formulation of claim 18, wherein $R_4$ is 2-ethylhexyl, linear octyl, or a mixture of these, and Z is S.

28. The formulation of claim 18, wherein n is 0 and Z is S.

29. The formulation of claim 25, wherein $R_4$ is 2-ethylhexyl, linear octyl, or a mixture of these, and Z is S.

30. The formulation of claim 25, wherein n is 0 and Z is S.

31. The formulation of claim 5, wherein $R_4$ is selected from the group consisting of butyl, 2-ethylhexyl, octyl, decyl, dodecyl, tetradecyl, and mixtures of any of these; Z is S; and $R_2$ and $R_3$ are both H.

32. The formulation of claim 10, wherein $R_4$ is selected from the group consisting of butyl, 2-ethylhexyl, octyl, decyl, dodecyl, tetradecyl, and mixtures of any of these; Z is S; and $R_2$ and $R_3$ are both H.

33. The formulation of claim 12, wherein $R_4$ is selected from the group consisting of butyl, 2-ethylhexyl, octyl, decyl, dodecyl, tetradecyl, and mixtures of any of these; Z is S; and $R_2$ and $R_3$ are both H.

* * * * *

UNITED STATES PATENT AND TRADEMARK OFFICE
CERTIFICATE OF CORRECTION

PATENT NO. : 7,341,985 B2 Page 1 of 1
APPLICATION NO. : 10/961763
DATED : March 11, 2008
INVENTOR(S) : Gauri Sankar Lal et al.

It is certified that error appears in the above-identified patent and that said Letters Patent is hereby corrected as shown below:

Column 22, Line 7

In claim 16 delete the word "0.00 1" and insert the word -- 0.001 --

Signed and Sealed this

Eighth Day of July, 2008

JON W. DUDAS
*Director of the United States Patent and Trademark Office*